(12) United States Patent
Fritz

(10) Patent No.: US 7,630,075 B2
(45) Date of Patent: Dec. 8, 2009

(54) CIRCULAR POLARIZATION ILLUMINATION BASED ANALYZER SYSTEM

(75) Inventor: Bernard S. Fritz, Eagan, MN (US)

(73) Assignee: Honeywell International Inc., Morristown, NJ (US)

( * ) Notice: Subject to any disclaimer, the term of this patent is extended or adjusted under 35 U.S.C. 154(b) by 420 days.

(21) Appl. No.: 11/554,878

(22) Filed: Oct. 31, 2006

(65) Prior Publication Data

US 2007/0058252 A1 Mar. 15, 2007

Related U.S. Application Data

(63) Continuation-in-part of application No. 11/306,508, filed on Dec. 30, 2005, which is a continuation-in-part of application No. 10/950,898, filed on Sep. 27, 2004, now Pat. No. 7,130,046.

(51) Int. Cl.
*G01N 21/00* (2006.01)
*G01J 4/00* (2006.01)

(52) U.S. Cl. .................. 356/337; 356/336; 356/364; 356/367; 356/368; 356/369

(58) Field of Classification Search ......... 356/335–343, 356/364–369, 317–319; 250/458.1, 459.1, 250/461.1, 461.2
See application file for complete search history.

(56) References Cited

U.S. PATENT DOCUMENTS 3,822,095 A 7/1974 Hirshfield
3,928,094 A 12/1975 Angell
3,976,862 A 8/1976 Curbelo
4,284,412 A 8/1981 Hansen et al.
4,478,076 A 10/1984 Bohrer
4,478,077 A 10/1984 Bohrer
4,501,144 A 2/1985 Higashi et al.
4,599,000 A 7/1986 Yamada
4,651,564 A 3/1987 Johnson et al.
4,683,159 A 7/1987 Bohrer et al.

(Continued)

FOREIGN PATENT DOCUMENTS

DE 10122321 4/2002

(Continued)

OTHER PUBLICATIONS de Grooth et al., "Light-Scattering Polarization Measurements as a New Parameter in Flow Cytometry," Cytometry 8: pp. 539-544, 1987.

(Continued)

*Primary Examiner*—Sang Nguyen
(74) *Attorney, Agent, or Firm*—Kris T. Fredrick

(57) ABSTRACT

A particle discriminator using circularly polarized light projected through a channel having target particles. Light may be propagated through the channel, with some light scattered separated into forward angle scattered light, small angle scattered light and unscattered light. The forward angle scattered light may be linearly polarized and detected. The small angle scattered light may be linearly polarized in a direction orthogonal to the direction of the polarization of the forward angle scattered light, and at least both these kinds of light may be detected. Data from these detected kinds of light may be analyzed to discriminate particles from one another.

23 Claims, 5 Drawing Sheets

U.S. PATENT DOCUMENTS

| | | | |
|---|---|---|---|
| 4,695,034 A | 9/1987 | Shimizu et al. | |
| 4,704,033 A | 11/1987 | Fay et al. | |
| 4,745,279 A | 5/1988 | Karkar et al. | |
| 4,818,263 A | 4/1989 | Mitch | |
| 4,874,949 A | 10/1989 | Harris et al. | |
| 4,911,616 A | 3/1990 | Laumann, Jr. | |
| 4,932,989 A | 6/1990 | Presby | |
| 4,957,363 A * | 9/1990 | Takeda et al. | 356/73 |
| 4,980,292 A | 12/1990 | Elbert et al. | |
| 5,017,497 A | 5/1991 | de Grooth et al. | |
| 5,050,429 A | 9/1991 | Nishimoto et al. | |
| 5,078,581 A | 1/1992 | Blum et al. | |
| 5,082,242 A | 1/1992 | Bonne et al. | |
| 5,085,562 A | 2/1992 | van Lintel | |
| 5,096,388 A | 3/1992 | Weinberg | |
| 5,108,623 A | 4/1992 | Cangelosi et al. | |
| 5,129,794 A | 7/1992 | Beatty | |
| 5,133,602 A * | 7/1992 | Batchelder et al. | 356/615 |
| 5,171,132 A | 12/1992 | Miyazaki et al. | |
| 5,176,358 A | 1/1993 | Bonne et al. | |
| 5,185,641 A | 2/1993 | Igushi et al. | |
| 5,194,909 A | 3/1993 | Tycko | |
| 5,219,278 A | 6/1993 | van Lintel | |
| 5,224,843 A | 7/1993 | van Lintel | |
| 5,244,537 A | 9/1993 | Ohnstein | |
| 5,323,999 A | 6/1994 | Bonne et al. | |
| 5,441,597 A | 8/1995 | Bonne et al. | |
| 5,452,878 A | 9/1995 | Gravesen et al. | |
| 5,457,526 A | 10/1995 | Kosaka | |
| 5,475,370 A * | 12/1995 | Stern | 340/583 |
| 5,510,267 A | 4/1996 | Marshall | |
| 5,528,045 A | 6/1996 | Hoffman et al. | |
| 5,570,193 A | 10/1996 | Landa et al. | |
| 5,601,080 A | 2/1997 | Oppenheimer | |
| 5,616,501 A | 4/1997 | Rodriguez et al. | |
| 5,633,724 A | 5/1997 | King et al. | |
| 5,683,159 A | 11/1997 | Johnson | |
| 5,716,852 A | 2/1998 | Yager et al. | |
| 5,717,631 A | 2/1998 | Carley et al. | |
| 5,719,399 A * | 2/1998 | Alfano et al. | 250/341.3 |
| 5,726,751 A | 3/1998 | Altendorf et al. | |
| 5,757,476 A | 5/1998 | Nakamoto et al. | |
| 5,760,900 A | 6/1998 | Ito et al. | |
| 5,793,485 A | 8/1998 | Gourley | |
| 5,799,030 A | 8/1998 | Brenner | |
| 5,822,170 A | 10/1998 | Cabuz et al. | |
| 5,836,750 A | 11/1998 | Cabuz | |
| 5,837,547 A | 11/1998 | Schwartz | |
| 5,839,807 A | 11/1998 | Perlo | |
| 5,863,502 A | 1/1999 | Southgate et al. | |
| 5,880,474 A | 3/1999 | Norton et al. | |
| 5,893,722 A | 4/1999 | Hibbs-Brennen et al. | |
| 5,901,939 A | 5/1999 | Cabuz et al. | |
| 5,922,210 A | 7/1999 | Brody et al. | |
| 5,932,100 A | 8/1999 | Yager et al. | |
| 5,948,684 A | 9/1999 | Weigl et al. | |
| 5,970,315 A | 10/1999 | Carley et al. | |
| 5,971,158 A | 10/1999 | Yager et al. | |
| 5,972,710 A | 10/1999 | Weigl et al. | |
| 5,974,867 A | 11/1999 | Forster et al. | |
| 6,007,775 A | 12/1999 | Yager | |
| 6,032,689 A | 3/2000 | Tsai et al. | |
| 6,054,335 A | 4/2000 | Sun et al. | |
| 6,067,157 A | 5/2000 | Altendorf | |
| 6,082,185 A | 7/2000 | Saaski | |
| 6,084,670 A * | 7/2000 | Yamazaki et al. | 356/343 |
| 6,091,197 A | 7/2000 | Sun et al. | |
| 6,091,537 A | 7/2000 | Sun et al. | |
| 6,094,293 A | 7/2000 | Yokoyama et al. | |
| 6,097,485 A | 8/2000 | Lievan | |
| 6,097,859 A | 8/2000 | Solgaard et al. | |
| 6,106,245 A | 8/2000 | Cabuz | |
| 6,109,889 A | 8/2000 | Zengerle et al. | |
| 6,116,756 A | 9/2000 | Peeters et al. | |
| 6,124,663 A | 9/2000 | Haake et al. | |
| 6,139,800 A | 10/2000 | Chandler | |
| 6,179,586 B1 | 1/2001 | Herb et al. | |
| 6,184,607 B1 | 2/2001 | Cabuz et al. | |
| 6,215,221 B1 | 4/2001 | Cabuz et al. | |
| 6,237,619 B1 | 5/2001 | Maillefer et al. | |
| 6,240,944 B1 | 6/2001 | Ohnstein et al. | |
| 6,249,341 B1 | 6/2001 | Basiji et al. | |
| 6,281,975 B1 | 8/2001 | Munk | |
| 6,320,656 B1 | 11/2001 | Ferrante et al. | |
| 6,370,407 B1 * | 4/2002 | Kroeger et al. | 600/319 |
| 6,382,228 B1 | 5/2002 | Cabuz et al. | |
| 6,549,275 B1 | 4/2003 | Cabuz et al. | |
| 6,597,438 B1 | 7/2003 | Cabuz et al. | |
| 6,721,051 B2 * | 4/2004 | Mengç et al. | 356/368 |
| 6,856,391 B2 * | 2/2005 | Garab et al. | 356/366 |
| 6,980,294 B2 * | 12/2005 | Namba et al. | 356/318 |
| 7,064,873 B2 * | 6/2006 | Lapstun et al. | 358/482 |
| 2003/0057968 A1 | 3/2003 | Wang et al. | |
| 2003/0142291 A1 | 7/2003 | Padmanabhan et al. | |
| 2004/0065143 A1 | 4/2004 | Husher | |
| 2004/0109386 A1 | 6/2004 | Gold et al. | |
| 2004/0154933 A1 | 8/2004 | Cosofret | |
| 2004/0233424 A1 | 11/2004 | Lee et al. | |
| 2005/0105077 A1 | 5/2005 | Padmanabhan et al. | |
| 2006/0066852 A1 | 3/2006 | Fritz et al. | |

FOREIGN PATENT DOCUMENTS

| | | |
|---|---|---|
| EP | 0269076 | 6/1988 |
| EP | 0694784 | 1/1996 |
| EP | 1001326 | 5/1999 |
| EP | 1134548 | 9/2001 |
| EP | 1359419 | 5/2003 |
| JP | 60082865 | 12/1983 |
| JP | 61066974 | 4/1986 |
| JP | 10073528 | 3/1998 |
| JP | 2000056228 | 2/2000 |
| JP | 2004257756 | 9/2004 |
| WO | 9316384 | 8/1993 |
| WO | 9527199 | 10/1995 |
| WO | 9960397 | 11/1999 |
| WO | 0109598 | 2/2001 |
| WO | 0210713 | 2/2002 |
| WO | 0210714 | 2/2002 |
| WO | 2004059316 | 7/2004 |
| WO | 2005090983 | 9/2005 |
| WO | 2005108963 | 11/2005 |
| WO | 2005114142 | 12/2005 |
| WO | 2005114144 | 12/2005 |
| WO | 2007000574 | 1/2007 |

OTHER PUBLICATIONS

Ost et al., "Flow Cytometric Differentiation of Erythrocytes and Leukocytes in Dilute Whole Blood by Light Scattering," Cytometry 32: pp. 191-197, 1998.

Salzman et al., "Cell Classification by Laser Light Scattering: Identification and Separation of Unstained Leukocytes," ACTA Cytologics, vol. 19 No. 3, pp. 374-377, Jul.-Aug. 1975.

HemoCue Hb 201+, Operating Manual, pp. 1-41, prior to Dec. 2006.

Lamvik et al., Nonlabeled Secondary Antibodies Augment/Maintain the Binding of Primary, Specific Antibodies to Cell Membrande Antigens, Cytometery 45, pp. 187-193, 2001.

http://www.micronics.net/tsensor.htm, pp. 1-4, downloaded Jun. 14, 2000.

http://www.micronics.net/hfilter.htm, pp. 1-3, downloaded Jun. 14, 2000.

http://www.micronics.net/mcytometry.htm, pp. 1-4, downloaded Jun. 14, 2000.

http://www.micronics.net/orcafluidics.htm, pp. 1-4, downloaded Jun. 14, 2000.

Altendorf et al, "Results Obtained Using A Prototype Microfluidics-Based Hematology Analyzer", SPIE Biomedical Optics 97, 1997.

Altendorf et al., "Differential Blood Cell Counts Obtained Using A Microchannel Based Flow Cytometer", Solid State Sensors & Actuators, vol. 1, 531, 1997.

Altendorf et al., "Implementation Of Novel Optical Detection Methods For Clinically Important Blood Analytes Using Microfabricated Flow Structures (T-Sensors™)", MicroTAS 98, Banff, Canada, Apr. 1998.

Altendorf et al., "Microfabrication Technology For Research And Diagnostics, Silicon Microchannel Optical Flow Cytometry", SPIE Proceedings, Biomedical Optics 96, Jan. 1996.

Cabuz et al., "Mesoscopic Sampler Based on 3D Array of Electrostatically Activated Diaphragms", The 10th Int. Conf. On Solid-State Sensors and Actuators, Transducers'99, Jun. 7-12, 1999, Sendai Japan, p. 1890-1.

Darling et al., "Integration Of Microelectrodes With Etched Microchannels For In-Stream Electrochemical Analysis", MicroTAS 98, Banff, Canada, Apr. 1998.

Fedder et al., "Laminated High-Aspect-Ratio Microstructures in a Conventional CMOS Process", Proc. Micro Electro Mechanical Systems Workshop, MEMS 96, San Diego, California, Feb. 11-15, 1996, pp. 13-18.

Hatch et al., "Microfluidic Approaches To Immunoassays", SPIE conference on Micromachining and Microfabrication Symposium at Santa Clara, CA, Sept. 20-22, 1999.

Huang et al., "Development Of A Flow Cytometry Based Miniature Chemical Fluid Analysis System Using Fluorescent Microbeads", SPIE Biomedical Optics, BIOS 97, conference proceedings, 1997.

Lehman et al., "High-Frequency Modulation Characteristics of Red VCSELs", Electronics Letters, Feb. 13, 1997, vol. 33(4), pp. 298-300. Copyright 1997 IEEE.

Ohnstein et al., "Micromachined Silicon Microvalve", Proceedings of MEMS, 1990, IEEE Micro Electromechanical Systems, Napa Valley, California, Feb. 11-14, 1990, pp. 95-98.

Roulet et al., "Fabrication of Multilayer Systems Combining Microfluidic and Microoptical Elements for Fluorescence Detection," Journal of Microelectromechanical Systems, vol. 10 No. 44, pp. 483-491, Dec. 4, 2001.

Shapiro, "Practical Flow Cytometry", third edition, 1995, p. 237.

Strzelecka et al., "Parallel Free-Space Optical Interconnect Based on Arrays of Vertical-Cavity Lasers and Detectors with Monolithic Microlenses", Applied Optics, v. 37(14), May 10, 1998, pp. 2811-2821. Copyright 1998 Optical Society of America.

Terstappen et al., "Four-Parameter White Blood Cell Differential Counting Based on Light Scattering Measurements", Alan R. Liss, Inc., Cytometery 9:39-43, 1988.

Toshiyoshi et al., "Micromechanical Lens Scanner for Fiber Optic Switches", Proc. 3rd International Conference on Micro Opto Electro Mechanical Systems (MOEMS 99), Aug. 30-Sep. 1, 1999, Mainz, Germany, pp. 165-170.

Toshiyoshi et al., "Surface micromachined 2D Lens Scanner Array", Proc. IEEE?LEOS International Coference on Optical EMMS/ Sheraton Kauai Resort, Kauai, Hawaii, Aug. 21-24, 2000, 3 pages.

Tuantranont et al., "Flip Chip Integration of Lenslet Arrays on Segmented Deformable Micromirrors", Part of the Symposium on Design, Test and Microfabrication of MEMS and MOEMS, Paris, France, Mar.-Apr. 1999, SPIE vol. 3680, 0277-786X/99, pp. 668-678.

Tuantranont et al., "MEMS-Controllable Microlens Array For Beam Steering and Precision Alignment in Optical Interconnect Systems", Solid-State Sensor and Actuator Workshop, Hilton Head Island, South Carolina, Jun. 4-8, 2000, pp. 101-104.

Weigl et al, "Silicon-Microfabricated Diffusion-Based Optical Chemical Sensor", Reprint from "Sensors & Actuators" B 38-39, 452-457, 1997I.

Weigl et al, "Microfluidic Diffusion-Based Separation And Detection", Science, vol. 283, pp. 346-347, Jan. 15, 1999.

Weigl et al, "Optical And Electrochemical Diffusion-Based Detection Of Analytes In Complex Samples Using Microfabricated Flow Structures (T-SensorSTM)", Micro- and nanofabn'cated electro-optical mechanical systems for biomedical and environmental applications II- SPIE vol. 3606, Jan. 25-26, 1999.

Weigl et al, "Simultaneous Self-Referencing Analyte Determination In Complex Sample Solutions Using Microfabricated Flow Structures (T-Sensors™)", Proceedings of MicroTAS 98, 81-4, Banff, Canada, 1998.

Weigl et al., "Diffusion-Based Optical Chemical Detection In Silicon Flow Structures", B. Weigl et al., Analytical Methods & Instrumentation, μTTAS 96 special edition, 1996.

Weigl et al., "Fluorescence And Absorbance Analyte Sensing In Whole Blood And Plasma Based On Diffusion Separation In Silicon-Microfabricated Flow Structures (T-Sensors™)", Biomedical Optics, vol. 6, No. 1, Jul. 1997.

Weigl et al., "Rapid Sequential Chemical Analysis Using Multiple Fluorescent Reporter Beads", μTTAS 96 Conference Proceedings, 1996.

Weigl, "Microfluidic Diffusion Based Electrochemical Detection Using Microfabricated Flow Structures (T-Sensors™)", Analytical Chemistry, submitted 1999.

Weigl, "Whole Blood Assays Using Microfluidics-Based T-SensorSTm Technology", Medical Design Online, http://news.medicaldesignonline.com/featuresarticles/19990416-5922.html, Apr. 1999.

Yager et al., "Applying Microfluidic Chemical Analytical Systems To Imperfect Samples", Micro Total Analysis Systems 98, D. Harrison & A. van den Berg (ed.), Kluwer Academic Publishers, Dordrecht, 207-212, 1998.

Yager et al., "Design Of Microfluidic Sample Preconditioning Systems For Detection Of Biological Agents In Environmental Samples", Yager, M. et al., SPIE Proceedings, 3515, 252-259, 1998.

* cited by examiner

CIRCULAR POLARIZATION ILLUMINATION BASED ANALYZER SYSTEM

This application is a continuation-in-part of U.S. patent application Ser. No. 11/306,508 filed Dec. 30, 2005, which is a continuation-in-part of U.S. patent application Ser. No. 10/950,898, filed Sep. 27, 2004 now U.S. Pat. No. 7,130,046. U.S. patent application Ser. No. 10/950,898, filed Sep. 27, 2004, is hereby incorporated by reference. U.S. patent application Ser. No. 11/306,508, filed Dec. 30, 2005, is hereby incorporated by reference.

BACKGROUND

The present invention pertains to particle detection and particularly to discriminating particles from one another into various groups. More particularly, the invention pertains to scattered light used to discriminate these particles.

The invention relates to U.S. patent application Ser. No. 11/380,878, filed on Apr. 28, 2006, which is hereby incorporated by reference. The invention relates to U.S. Pat. No. 5,837,547, issued on Nov. 17, 1998, which is hereby incorporated by reference. The invention relates to U.S. Pat. No. 5,017,497, issued May 21, 1991, which is hereby incorporated by reference.

SUMMARY

The invention is a system that uses polarized light to discriminate particles from one another.

DESCRIPTION

Discrimination of various kinds of particles with light is a technique useful for analyses of such things as white blood cells (WBCs). For an illustrative example, WBC measurement in a cytometer may consist of discriminating the five forms of WBCs with a counting of particles in each group. The five kinds of WBCs or leukocytes include three kinds of granulocytes—neutrophils, eosinophils and basophils, and two kinds of leukocytes without granules in their cytoplasm—lymphocytes and monocytes. The present system provides an enhancement to a forward angle light scattering/small angle light scattering approach of light scattered off the WBCs that may show a complete separation in plotted data.

Birefringence of particles may provide a basis of discrimination of various kinds of particles for grouping, such as WBCs. By using polarized light, one can measure the effects that individual particles may reveal by the incident polarized light. Such effects appear useful for discriminating various particles from one another. Circular polarized light may be used in the present system to impinge particles which in turn scatter such light. FALS and SALS detectors, having linear polarizers orthogonally situated relative to each other in terms of a polarization state or direction, before them, may detect such light to provide data in the form of, for instance, scattergrams, with information discriminating various kinds of particles apart from one another.

The present system goes beyond a depolarization measurement approach of particles, such as WBCs, where a ninety degree angle scattering of light that is polarized naturally with a measurement being the extent that the light is unpolarized or depolarized. A distinguishing characteristic of the present system is a use of circularly polarized light to impinge a target, having orthogonal polarizers between the target and detectors for detecting small angle (i.e., of about or less than 20 degrees) and forward angle light (i.e. of about or less than 5 degrees), respectively, scattered from the target. Small angle scattered light, forward angle scattered light, and unscattered light may be defined in terms of angles having magnitudes other than those illustratively stated herein.

Figure 1A:
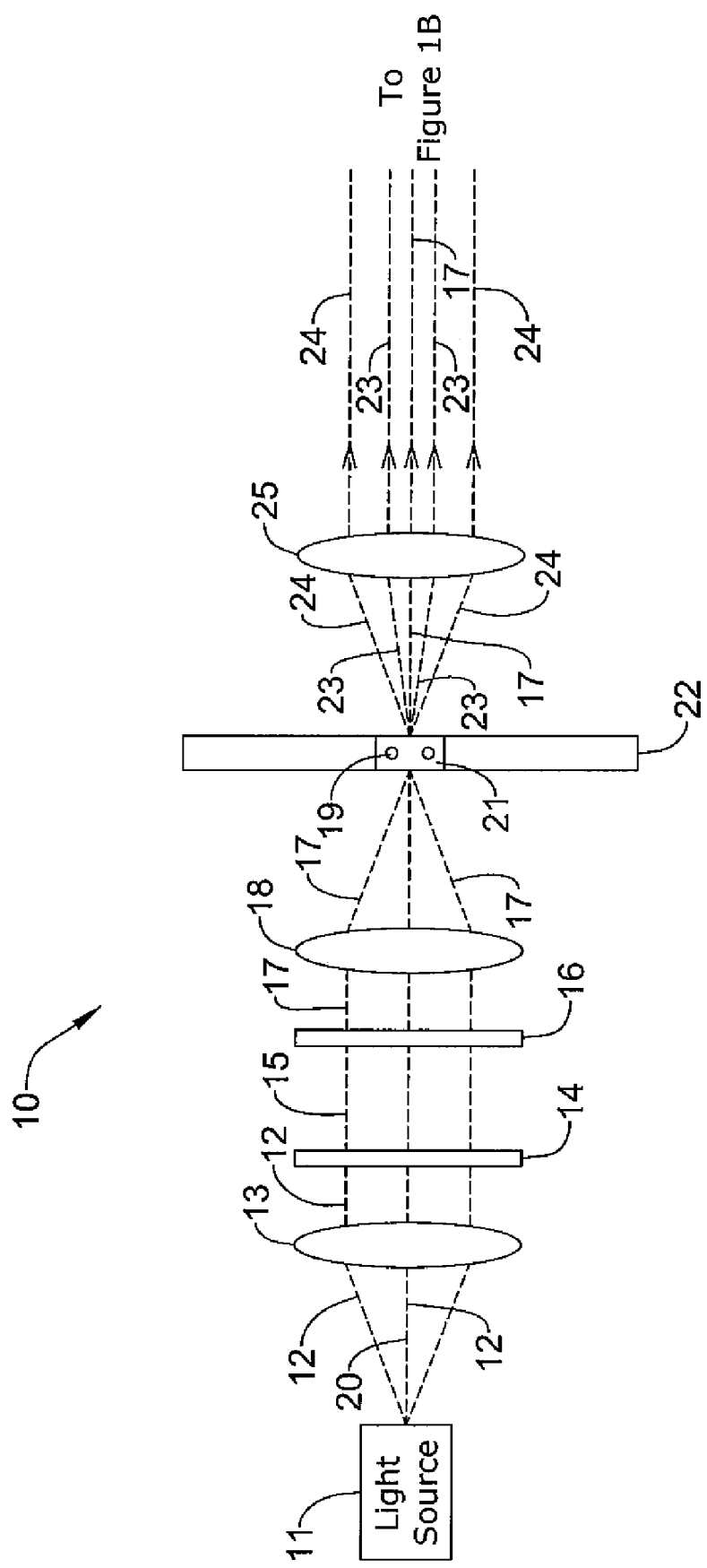
FIG. 1 is a diagram of the circular polarization illumination based analyzer system.
Figure 1B:
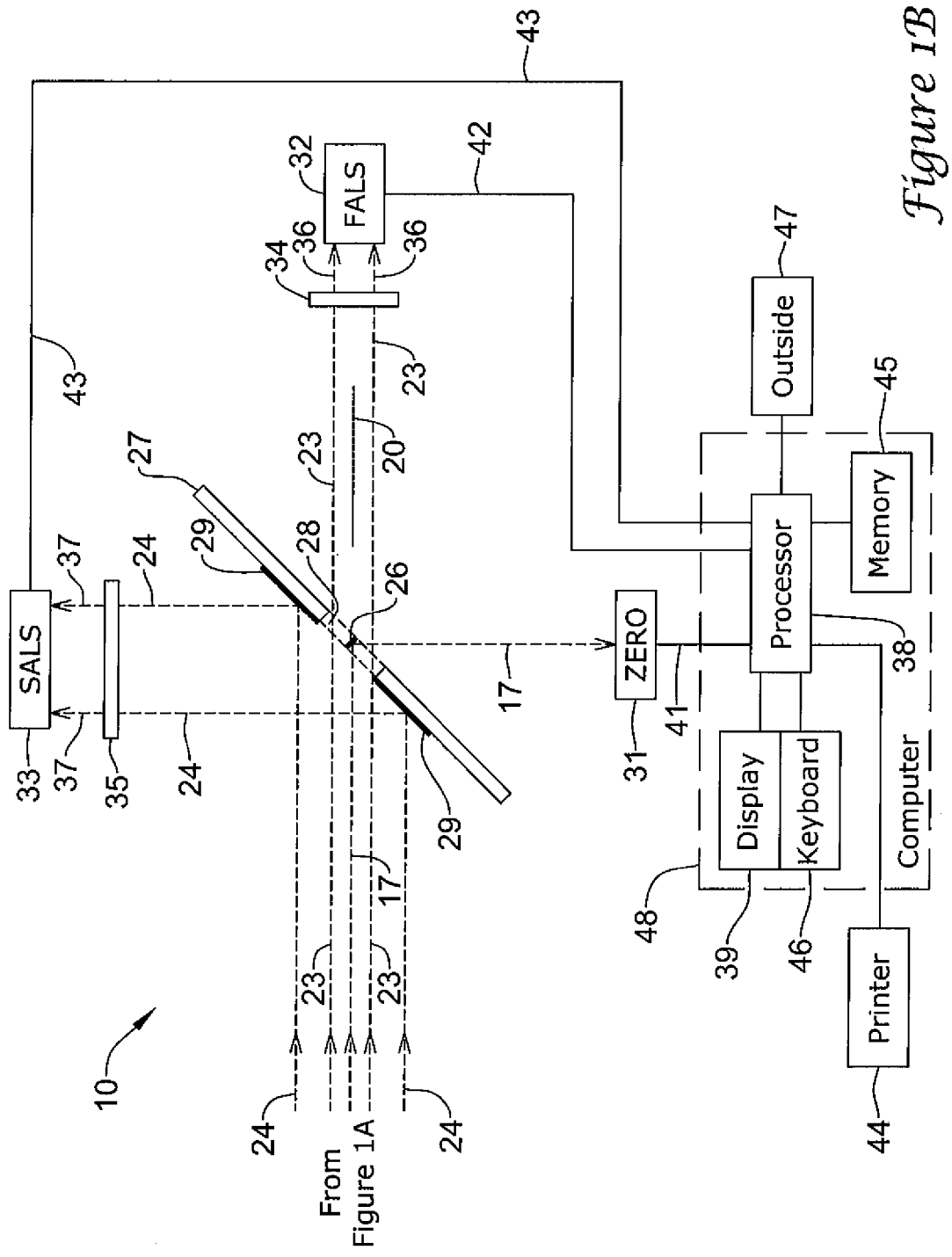

FIG. 1 shows a particle discrimination system 10. A light source 11 may emanate a light 12 through a collimating lens 13. Light 12 may proceed through a linear polarizer 14. Polarized light 15 may proceed through a quarter-wave plate 16 which converts the linearly polarized light 15 into circularly polarized light 17. Alternatively, light source 11 may emanate linearly polarized 15 or circularly polarized light 17, thereby eliminating polarizer 14 or polarizers 14 and 16, respectively. Light 17 may proceed through a lens 18 to be focused on particles 19 in a channel or receptacle 21 of a card 22. Some of the light 17 may impinge particles 19 and be scattered into light 23 and 24. Other light 17 might not be scattered. Light 24 may be the result of small angel light scattering by the particles in the channel. Light 23 may be the result of forward angle light scattering by the particles. The angle range of scattering of light 23 may be between about one and five degrees relative to the optical axis 20 of the system 10. The angle range of scattering of light 24 may be between about five and twenty degrees relative to the optical axis 20. The light 17, which is effectively non-scattered, may be light between zero and about one degree relative to the optical axis. These ranges may be predetermined and adjusted as desired to obtain certain performance from system 10.

Light 17, 23 and 24 may be collimated by a lens 25. Light 17 may proceed approximately along the optical axis 20 to a mirror 26 situated in a structure 27. The mirror 26 may have a generally flat reflective surface which is situated at about a 45 degree angle counterclockwise relative to the optical axis 20. The light 17 may be reflected by mirror 26 to a zero detector 31. Detector 31 may indicate an amplitude or intensity of light 17 impinging it at about the same time of the impingement.

Light 23 may proceed through a circular opening or hole 28 of structure 27. The opening 28 may be concentric relative to the location of mirror 26. Light 23 of a scatter angle greater than one degree may miss the mirror 26 as it proceeds through opening 28. Light 23 may go through a linear polarizer 34 to become linearly polarized light 36, which may be detected by a FALS detector 32. Similar to detector 31, detector 32 may indicate the amplitude or intensity of the light 36 impinging it at about the same time of the impingement. The opening 28 may be small enough to prevent light coming through scattered at an angle not greater than about five degrees. This angle may be adjusted as desired by varying the hole diameter.

Light 24 may proceed on toward structure 27 but impinge structure 27 since the light has a scatter angle greater than about five degrees. Structure 27 may be a beam separator having a reflective surface 29. Reflective surface 29 may annular and concentric to the opening or hole 28. Surface 29 may extend from the outer edge of the opening 28 and extend outward a certain dimension resulting in the shape of a ring or circular band on the surface of structure 27 facing the incoming light 24. The width of the ring or annular band of reflective surface 29 may be such as to reflect light 24 having a scatter angle between about five and twenty degrees relative to the optical axis 20. The dimensions of surface 29 may be changed to reflect light of other scatter angles.

Reflective surface 29 may be positioned at about 45 degrees in a clockwise direction relative to the optical axis 20. Surface 29 may reflect the light 24 through a linear polarizer 35 to become linearly polarized light 37, which may be detected by a SALS detector 33. Similar to detectors 31 and 32, detector 33 may indicate the amplitude or intensity of light 37 impinging it at about the same time of the impingement.

Linear polarizer 14 may polarize light 12 in one direction, and the quarter-wave plate 16 may provide counter-clockwise or clockwise polarization of light 15 from a perspective of facing the cartridge 22 on the light source 11 side. The channel 21 may have a flow direction in the up, down, in or out, relative to the drawing sheet surface of FIG. 1. Polarizer 34 may polarize light 23 in one direction or another while facing the FALS detector 32. Polarizer 35 may polarize light 24 in another direction or so, while facing the SALS detector 33. However, the polarization directions or states of the linear polarizers 34 and 35 may be approximately orthogonal relative to each other.

The output signals 41, 42 and 43 of detectors 31, 32 and 33, respectively, may go to a processor 38 for converting signals into data about particles 19 in the channel 21 of card 22. Various particles 19 may be discriminated from one another. Data, calculations and graphs, such as scattergrams, may be provided to display 39. The displayed items may be printed out by a printer 44. Also, these items may be saved in a memory 45 and/or sent out to various destinations (outside 47) external to system 10. The processor 38 may receive information from the outside 47 to assist in processing the data provided by signals 41, 42 and 43. Also, a keyboard 46 may provide an interface for a user to analyze data about particles 19, provide desired formats of processed data, and communicate both ways with the outside 47, such as the internet. A computer 48 may be used for providing the processor 38, memory 45, keyboard 46, display 39, and more.

Figure 2A:
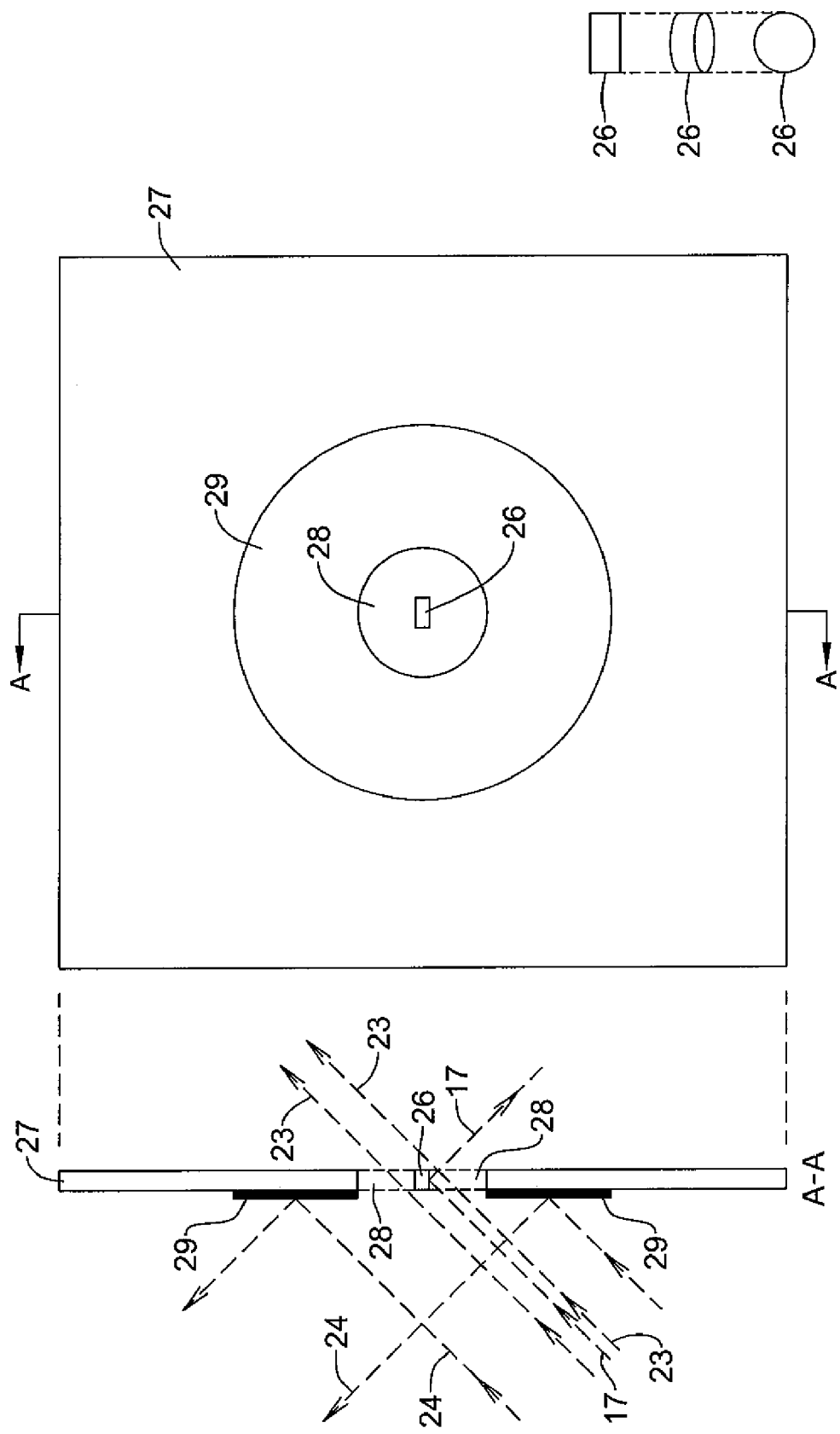
FIG. 2a is a diagram showing edge and front views of a beam separator of the analyzer system.

FIG. 2a shows an edge view and a face view of structure 27. Reflective disk surface 29 with an opening or hole 28 in the center of surface 29 and structure 27 is shown. The light rays 17, 23 and 24 are shown even though the light rays and structure 27 are rotated 45 degrees clockwise to be aligned with the face view of structure 27 for illustrative purposes.

The outside diameter of opening 28 may be about 4 to 5 millimeters. The outside diameter of the reflective disk may be about 8 to 10 millimeters. These dimensions may vary and depend on the placement of the various components such as the source 11, lenses 13, 18, and 25, polarizers 14, 16, 34 and 35, flow channel 21, and detectors 31, 32 and 33. The dimensions may also depend on focal lengths of the lenses. Other factors such as resolution, channel 21 size, design and layout of system 10 components may affect the dimensions.

Figure 2B:
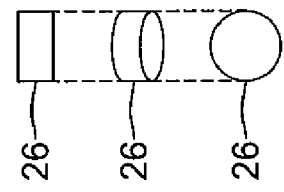
FIG. 2b shows various views of a center mirror of the beam separator.

FIG. 2b shows various views of mirror 26. The reflective surface of mirror 26 may be approximately perpendicular to the reflective surface 29 on structure 27. The top view of mirror 26 is an edge view like that shown in FIG. 2a. The reflective surface of mirror 26 may face down towards the lower left part of the drawing sheet. The middle view is a perspective of mirror 26. The bottom view is a face view of mirror 26. The diameter of mirror 26 may be about one millimeter. This dimension also may depend on the other dimensions and characteristics of system 10.

Light source 11 may be a laser diode or a similar device. If light source 11 emanates linearly polarized light, then linear polarizer 14 is not needed. If light source 11 emanates circularly polarized light, then polarizers 14 and 16 are not needed.

Polarizers 34 and 35 may polarize light about 90 degrees apart from each other in direction or state, or orthogonally relative to each other. Polarizer 34 may have a zero degree state or direction of polarization while polarizer 35 has about a ninety degree state or direction of polarization. For instance, if one polarizer polarizes in the X direction, the other polarizer may polarize in the Y direction.

Effectively, the channel 21 may be illuminated with circularly polarized light 17. One may look at the orthogonal polarization states at two of the output channels, i.e., FALS detector 32 and SALS detector 33. The zero detector 31 detecting light 17 at about a zero to one degree angle relative to the system optical axis 20 may have a maximum signal indication when there are no particles 19 in channel 21, i.e., there is no disturbance of the light 17 while propagating through channel 21. The flow channel 21 should be polarization free in terms of its effect on light going through it. If the particles 19 in channel 21 are birefringent, then a difference of signals may be seen in detectors 32, 33 and 31. Detector 31 may be regarded as one for an extinction channel having no scattered light. Detector 31 may provide counts of particles. The outputs of the FALS and SALS detectors 32 and 33, respectively, may be plotted as graphs which may be regarded as scattergrams. The scattergrams may include SALS versus FALS data plotting of the particles. The scattergrams of particles such as white blood cells (WBCs) may provide a count and differentiation of four groups of the WBCs. These polarized light-based scattergrams may provide a better distinction and indication of the four groups of WBCs than non-circularly polarized light illuminated WBCs. A linear polarization of the circularly polarized light scattered by the cell and detected for scattergrams, show the various groups of the cells being pulled further apart from one another in the scattergrams. Also, a fifth group of WBCs (basophils) may be distinguished if a number of such cells in the illuminated sample is sufficient.

Figure 3A:
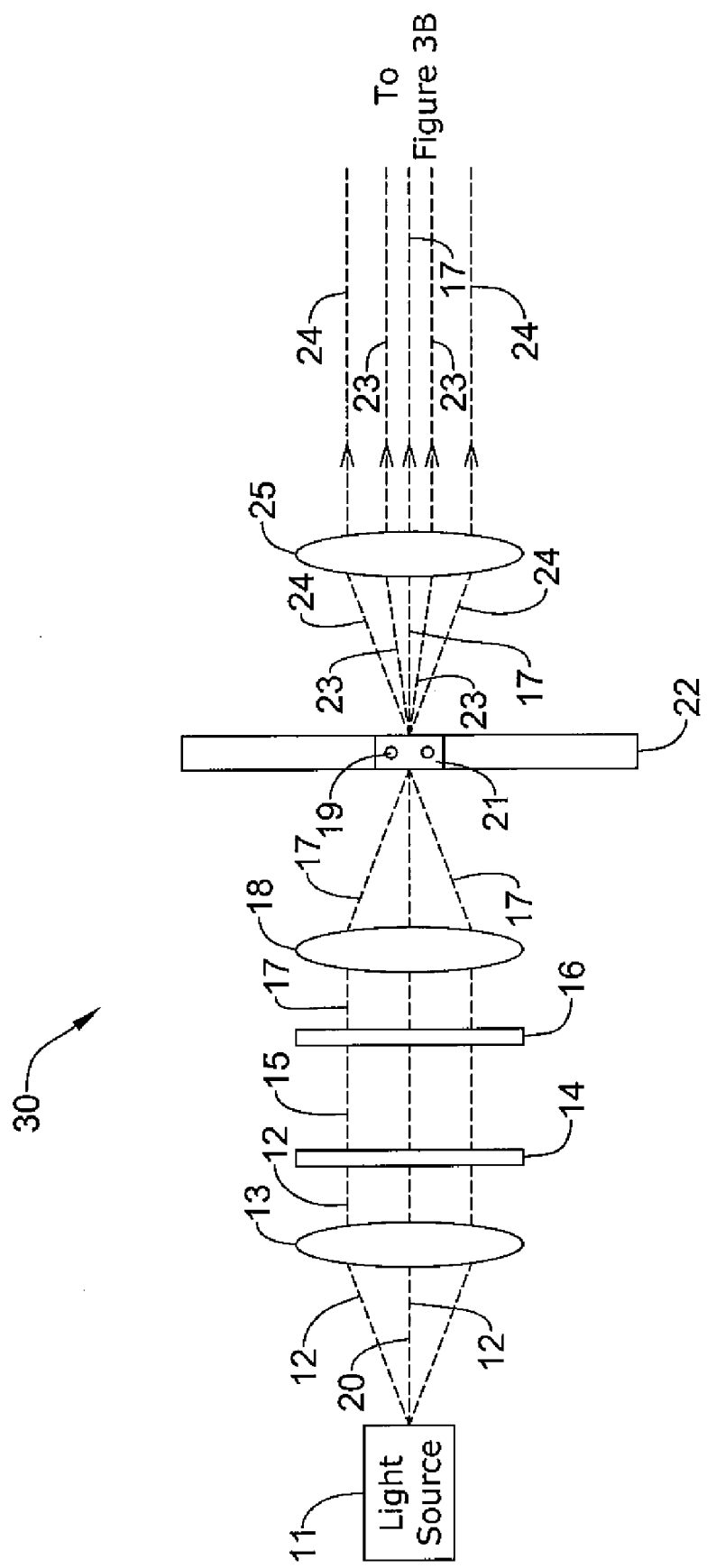
FIG. 3 is a diagram of the analyzer system of FIG. 1 having an extended detection mechanism.
Figure 3B:
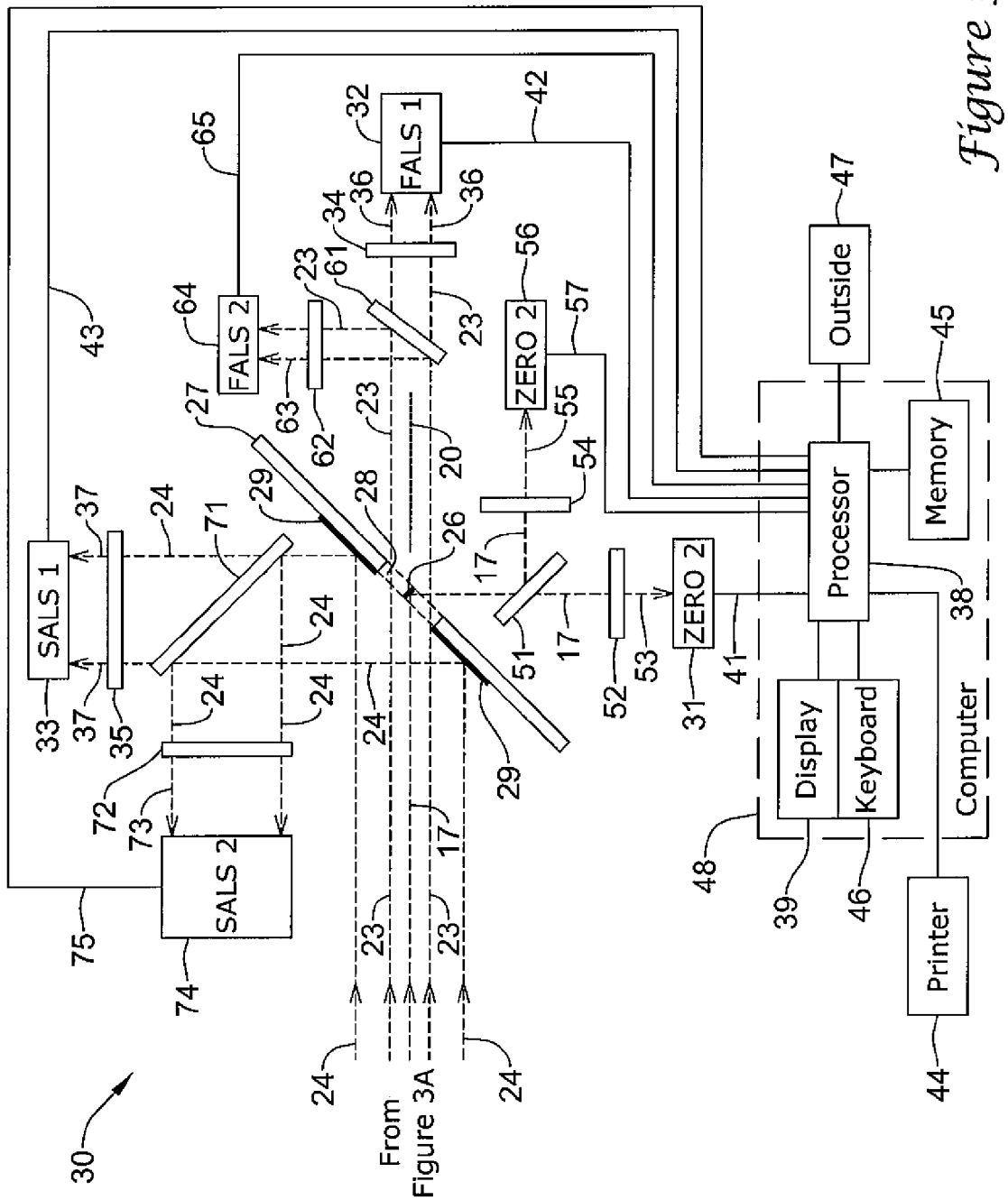

FIG. 3 shows an analyzer 30 like system 10 of FIG. 1 but having an extended detector arrangement. For instance, some non-scattered light 17 from mirror 26 may proceed through a light splitter 51 and a linear polarizer 52. From polarizer 52, a polarized light 53 may go to a zero 1 detector 31 which outputs an electrical signal 41 representing the light 53. Signal 41 may go to processor 38. Some light 17 may be reflected by splitter 51 through a linear polarizer 54. From polarizer 54, a polarized light 55 may proceed to a zero 2 detector 56 which outputs an electrical signal 57 representing the light 55. Signal 57 may go to processor 38. Linear polarizer 54 may be orthogonal relative to linear polarizer 52, in terms of polarizing. Processor 38 may compare and/or analyze signals 41 and 57 of the unscattered light 53 and 55, respectively, which can have linear polarizations orthogonal to each other, and determine birefringent effects, if any. Light 53 and 55 may be utilized for calibration and/or compensation of the system 30 analyzer.

A similar arrangement may be implemented in the FALS and SALS detection mechanisms. For instance, forward angle scattered light 23 may proceed through hole 28 to a splitter 61. Some of the light 23 may proceed through splitter 61 and a linear polarizer 34. From polarizer 34, polarized light 36 may go to a FALS 1 detector 32. An electrical signal 42 representing polarized light 36 may go from detector 32 to processor 38. Some of the light 23 may be reflected by splitter 61 through a linear polarizer 62. From polarizer 62, a polarized light 63 may go to a FALS 2 detector 64. Linear polarizer 62 may be orthogonal relative to linear polarizer 34, in terms of polarizing. Depending on the system design, polarizer 34 may or may not be orthogonal to polarizer 52, in terms of polarizing. An electrical signal 65 representing light signal 63 may go from detector 64 to processor 38. Processor 38 may compare and/or analyzer signals 42 and 65 and determine birefringent effects on light 23, such as non-symmetrical birefringence affecting forward angle scattered light 23 from channel 21. Light 36 and 63 may be utilized for calibration and/or compensation purposes of the system 30 analyzer.

In another instance, small angle scattered light 24 may be reflected by surface 29 to a splitter 71. Some of the light 24 may proceed through splitter 71 to a linear polarizer 35. From polarizer 35, a polarized light 37 may proceed to a SALS 1 detector 33. An electrical signal 43 representing the linearly polarized light 37 may go from detector 33 to processor 38. Some light 24 may be reflected by splitter 71 to a linear polarizer 72. From polarizer 72, a polarized light 73 may go to a SALS 2 detector 74. An electrical signal 75 representing light 73 may go from detector 74 to processor 38. In terms of polarizing, linear polarizer 72 may be orthogonal relative to polarizer 35, and polarizer 35 may be orthogonal to polarizer 34. In some designs, polarizer 35 might not be orthogonal to polarizer 34, in terms of polarization. Processor 38 may compare and/or analyzer signals 43 and 75 and determine birefringent effects on light 24, such as non-symmetrical birefringence affecting the small angle scattered light from channel 21. Light 37 and 73 may be utilized for calibration and/or compensation purposes of the system 30 analyzer.

Processor 38 may process signals 41, 57, 42, 65, 43 and 75 to establish data about particles 19 in channel 21, such as groups of various sized, shaped, textured, and so forth, particles, including counts. An example is differentiating the various kinds or groups of white blood cells. Processor 38 computation and analysis may be performed with information from the outside 47. Also, information may be sent by processor 38 to the outside 47 for further analysis and study.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A polarization based analyzer system comprising:
a light source;
a first polarizer situated at an output of the light source;
a channel;
a first optical mechanism for focusing light from the polarizer to the channel;
a second optical mechanism for collimating light from the channel;
a structure for directing a first light from the second optical mechanism in a first direction and a second light from the second optical mechanism in a second direction;
a first detector for detecting the first light;
a second detector for detecting second light;
a second polarizer situated between the structure and the first detector; and
a third polarizer situated between the structure and the second detector.

2. The system of claim 1, wherein:
the light source is for emanating linearly polarized light;
the first polarizer is a circular polarizer;
the second polarizer is a first linear polarizer; and
the third polarizer is a second linear polarizer.

3. The system of claim 2, wherein a polarization state of the second linear polarizer is approximately orthogonal to a polarization state of the second linear polarizer.

4. The system of claim 3, wherein:
the first light comprises forward angle scattered light; and
the second light comprises small angle scattered light.

5. The system of claim 4, further comprising:
a computer connected to the first and second detectors; and
wherein:
the forward angle scattered light is some of the first light scattered by particles in the channel;
the small angle scattered light is some of the second light scattered by particles in the channel;
the computer processes data from the first and second detectors into small angle scatter light versus forward angle scatter light graphs; and
the graphs provide groupings of the particles according to at least one feature that distinguish particles from one another.

6. The system of claim 4, wherein:
the structure comprises a first portion, a second portion and a third portion;
wherein:
the first portion is transmissive;
the second portion is reflective; and
the third portion is reflective;
the first portion is for transmitting the first light; and
the second portion is for reflecting the second light; and
the third portion is for reflecting a third light in a third direction.

7. The system of claim 1, wherein the channel is of a cytometer.

8. A method for discriminating particles, comprising:
projecting circularly polarized light through a receptacle for particles;
collimating the light that has been projected through the receptacle;
separating the light into small angle scattered light and forward angle scattered light;
linearly polarizing the forward angle scattered light;
linearly polarizing the small angle scattered light orthogonally relative to the polarized forward angle scattered light; and
analyzing the polarized forward angle scattered light and the polarized small angle scattered light to discriminate particles that being in the receptacle.

9. The method of claim 8, further comprising:
converting the polarized forward angle scattered light into a first type of electronic signals;
converting the polarized small angle scattered light into a second type of electronic signals; and
processing the first and second types of electronic signals into data representing various particles that being in the receptacle.

10. The method of claim 8, wherein the receptacle is a flow channel of a cytometer.

11. A circularly polarized illumination-based analyzer comprising:
a circularly polarized light source;
a first light splitter;
a channel situated between the light source and the first light splitter; and a first linear polarizer proximate to the light splitter;
a second linear polarizer proximate to the first light splitter and having a polarization direction approximately orthogonal to a polarization direction of the first linear polarizer;
a first detector proximate to the first linear polarizer;
a second detector proximate to the second linear polarizer;
the first light splitter for separating light from the channel into small angle scattered light, forward angle scattered light, and unscattered light;
the first linear polarizer for polarizing forward angle scattered light; and
the second linear polarizer is for polarizing small angle scattered light.

12. The analyzer of claim 11, further comprising:
a third detector proximate to the channel; and
wherein the third detector is for detecting unscattered light.

13. The analyzer of claim 11, further comprising:
a second light splitter situated between the first light splitter and the first polarizer;
a third detector proximate to the second light splitter;
a third linear polarizer situated between the second light splitter and the third detector;
a third light splitter situated between the first light splitter and the second linear polarizer;
a fourth detector proximate to the third light splitter; and
a fourth linear polarizer situated between the third light splitter and the fourth detector; and
wherein:
the third linear polarizer is orthogonal relative to the first linear polarizer; and
the fourth linear polarizer is orthogonal relative to the second linear polarizer.

14. A polarization based analyzer system comprising:
a light source;
a first polarizer situated at an output of the light source;
a channel;
a first optical mechanism for focusing light from the polarizer to the channel;
a second optical mechanism for collimating light from the channel;
a structure for directing a first light from the second optical mechanism in a first direction and a second light from the second optical mechanism in a second direction;
a first detector for detecting the first light;
a second detector for detecting second light;
a second polarizer situated between the structure and the first detector; and
a third polarizer situated between the structure and the second detector; and
wherein:
the light source is for emanating linearly polarized light;
the first polarizer is a circular polarizer;
the second polarizer is a first linear polarizer;
the third polarizer is a second linear polarizer;
a polarization state of the second linear polarizer is approximately orthogonal to a polarization state of the second linear polarizer;
the first light comprises forward angle scattered light;
the second light comprises small angle scattered light;
the structure comprises a first portion, a second portion and a third portion;
the first portion is transmissive;
the second portion is reflective;
the third portion is reflective;
the first portion is for transmitting the first light;
the second portion is for reflecting the second light; and
the third portion is for reflecting a third light in a third direction.

15. The system of claim 14, further comprising:
a third detector for detecting the third light; and
wherein the third light is unscattered light.

16. The system of claim 14, wherein:
the second portion is a ring-like band having borders that are different sized concentric circles;
the first portion is situated within the smaller concentric circle; and
the third portion is situated within the first portion.

17. A polarization based analyzer system comprising:
a light source;
a first polarizer situated at an output of the light source;
a channel;
a first optical mechanism for focusing light from the polarizer to the channel;
a second optical mechanism for collimating light from the channel;
a structure for directing a first light from the second optical mechanism in a first direction and a second light from the second optical mechanism in a second direction;
a first detector for detecting the first light;
a second detector for detecting second light;
a second polarizer situated between the structure and the first detector; and
a third polarizer situated between the structure and the second detector; and
wherein the channel is of a cytometer.

18. A method for discriminating particles, comprising:
projecting circularly polarized light through a receptacle for particles;
collimating the light that has been projected through the receptacle;
separating the light into small angle scattered light and forward angle scattered light;
linearly polarizing the forward angle scattered light;
linearly polarizing the small angle scattered light orthogonally relative to the polarized forward angle scattered light;
analyzing the polarized forward angle scattered light and the polarized small angle scattered light to discriminate particles that being in the receptacle;
converting the polarized forward angle scattered light into a first type of electronic signals;
converting the polarized small angle scattered light into a second type of electronic signals; and
processing the first and second types of electronic signals into data representing various particles that being in the receptacle.

19. The method of claim 18, further comprising:
plotting the data representing the signals into plots; and
analyzing the plots to classify the particles into several groups.

20. A method for discriminating particles, comprising:
projecting circularly polarized light through a receptacle for particles;
collimating the light that has been projected through the receptacle;
separating the light into small angle scattered light and forward angle scattered light;
linearly polarizing the forward angle scattered light;
linearly polarizing the small angle scattered light orthogonally relative to the polarized forward angle scattered light; and analyzing the polarized forward angle scattered light and the polarized small angle scattered light to discriminate particles that being in the receptacle; and wherein the receptacle is a flow channel of a cytometer.

21. A circularly polarized illumination-based analyzer comprising:
   a circularly polarized light source;
   a first light splitter;
   a channel situated between the light source and the first light splitter; and
   a first linear polarizer proximate to the light splitter;
   a second linear polarizer proximate to the first light splitter and having a polarization direction approximately orthogonal to a polarization direction of the first linear polarizer;
   a first detector proximate to the first linear polarizer; and
   a second detector proximate to the second linear polarizer; and
   wherein:
   the first light splitter is for separating light from the channel into small angle scattered light, forward angle scattered light, and unscattered light;
   the first linear polarizer is for polarizing forward angle scattered light; and
   the second linear polarizer is for polarizing small angle scattered light; and
   further comprising:
   a second light splitter situated between the first light splitter and the first polarizer;
   a third detector proximate to the second light splitter;
   a third linear polarizer situated between the second light splitter and the third detector;
   a third light splitter situated between the first light splitter and the second linear polarizer;
   a fourth detector proximate to the third light splitter; and
   a fourth linear polarizer situated between the third light splitter and the fourth detector; and
   wherein:
   the third linear polarizer is orthogonal relative to the first linear polarizer; and
   the fourth linear polarizer is orthogonal relative to the second linear polarizer.

22. The analyzer of claim 21, further comprising:
   a fifth detector proximate to the first light splitter;
   a fifth linear polarizer situated between the fifth detector and the first light splitter;
   a fourth light splitter situated between the fifth linear polarizer and the first detector;
   a sixth detector proximate to the fourth light splitter; and
   a sixth linear polarizer situated between the sixth detector and the fourth light splitter; and
   wherein:
   the fifth detector is for detecting unscattered light;
   the sixth detector is for detecting unscattered light; and
   the sixth linear polarizer is orthogonal relative to the fifth linear polarizer.

23. The analyzer of claim 22, further comprising:
   a processor connected to the first, second, third, fourth, fifth and sixth detectors; and
   the processor processes signals from the first, second, third, fourth, fifth and sixth detectors into data for discriminating particles in the channel.

* * * * *

UNITED STATES PATENT AND TRADEMARK OFFICE
CERTIFICATE OF CORRECTION

PATENT NO. : 7,630,075 B2 Page 1 of 1
APPLICATION NO. : 11/554878
DATED : December 8, 2009
INVENTOR(S) : Bernard S. Fritz It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 458 days.

Signed and Sealed this

Second Day of November, 2010

David J. Kappos
*Director of the United States Patent and Trademark Office*